United States Patent [19]

Takami et al.

[11] Patent Number: 4,596,132

[45] Date of Patent: Jun. 24, 1986

[54] GAS COMPONENT DETECTING PLUG

[75] Inventors: Akio Takami, Kounan; Toshitaka Matsuura, Komaki; Nobuo Kawai, Nagoya; Toshihiko Kimura, Aichi, all of Japan

[73] Assignee: NGK Spark Plug Co., Ltd., Nagoya, Japan

[21] Appl. No.: 665,359

[22] Filed: Oct. 26, 1984

[30] Foreign Application Priority Data

Oct. 26, 1983 [JP] Japan .................................. 58-200181

[51] Int. Cl.$^4$ ............................................. G01N 27/12
[52] U.S. Cl. .......................................... 73/23; 338/34
[58] Field of Search .................... 73/23, 27 R; 338/34; 340/634; 422/98; 204/424, 431

[56] References Cited

U.S. PATENT DOCUMENTS

| 4,206,173 | 6/1980 | Yamaguchi et al. | 73/27 R |
| 4,308,518 | 12/1981 | Hattori et al. | 73/27 R |
| 4,401,967 | 8/1983 | Miwa et al. | 73/27 R |
| 4,442,420 | 4/1984 | Novak | 338/34 |

FOREIGN PATENT DOCUMENTS 0101249 2/1984 European Pat. Off. .
2075690 11/1981 United Kingdom .

Primary Examiner—Stephen A. Kreitman
Attorney, Agent, or Firm—Oblon, Fisher, Spivak, McClelland & Maier

[57] ABSTRACT

A gas component detecting plug including a gas component-sensitive element, lead wires connected to the gas component-sensitive element, a tubular or board-like insulator which supports both the gas component-sensitive element and the lead wires, and an enclosure, the insulator being sealed to the enclosure so that the gas component-sensitive element is positioned on a leg portion side, characterized in that a spacer is disposed and retained in a gap formed between the insulator and the enclosure, in that a space on a head portion side formed by the insulator, enclosure, spacer and electrode wires is filled with glass and in that a rubbery elastic member having an insulating property is inserted in the head portion side. The gas component detecting plug is superior in water-proofness, gas-tightness, heat insulating property and productivity.

12 Claims, 8 Drawing Figures

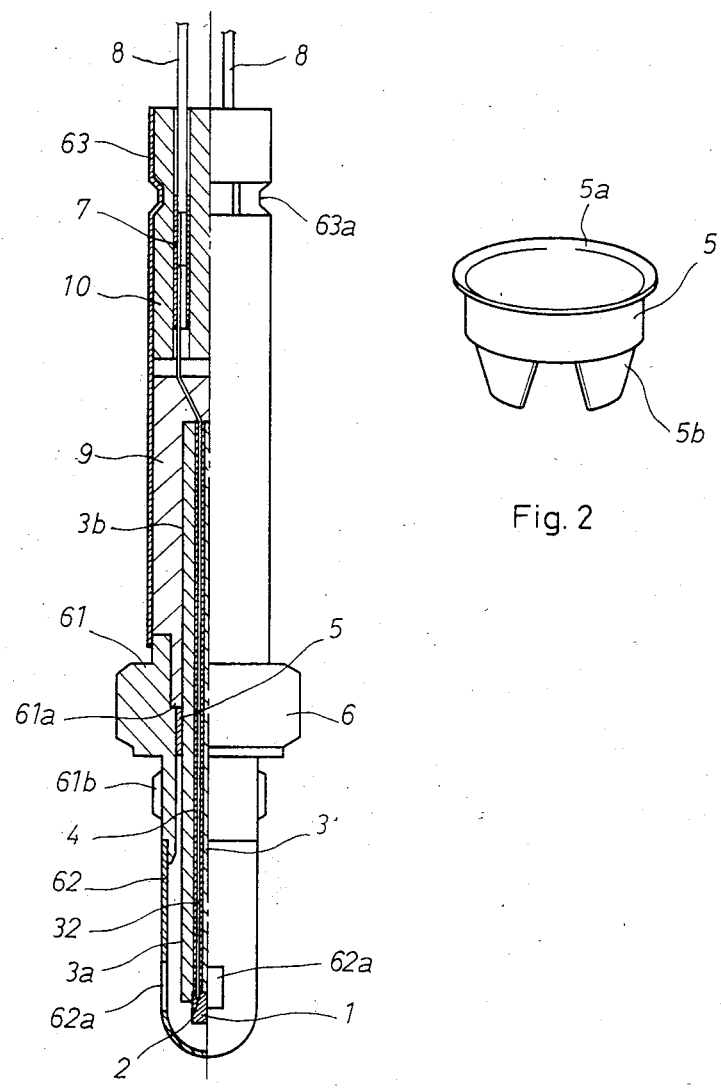

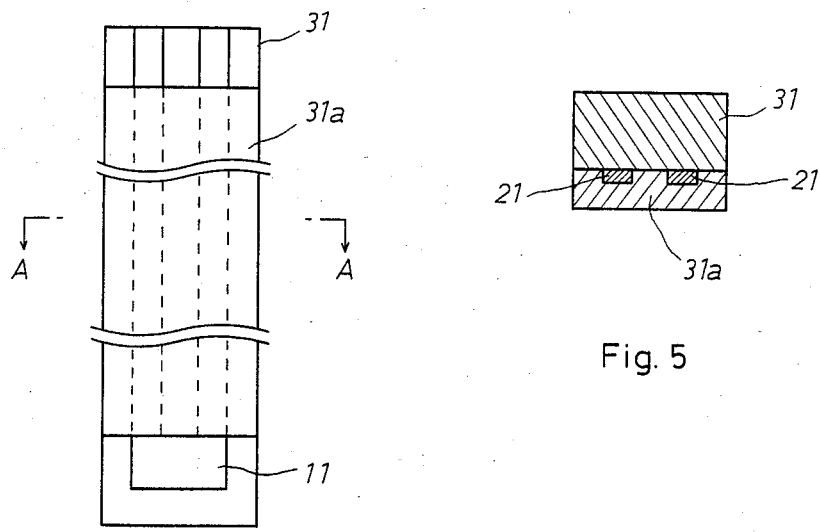
Fig. 4
Fig. 5
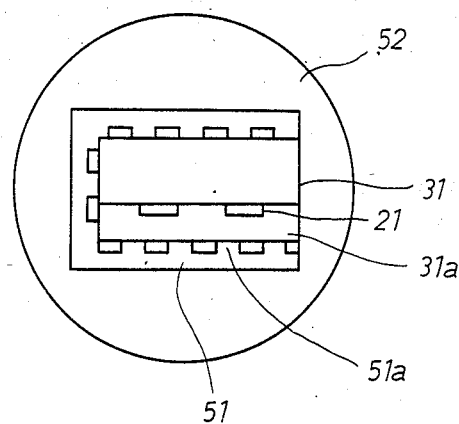
Fig. 6

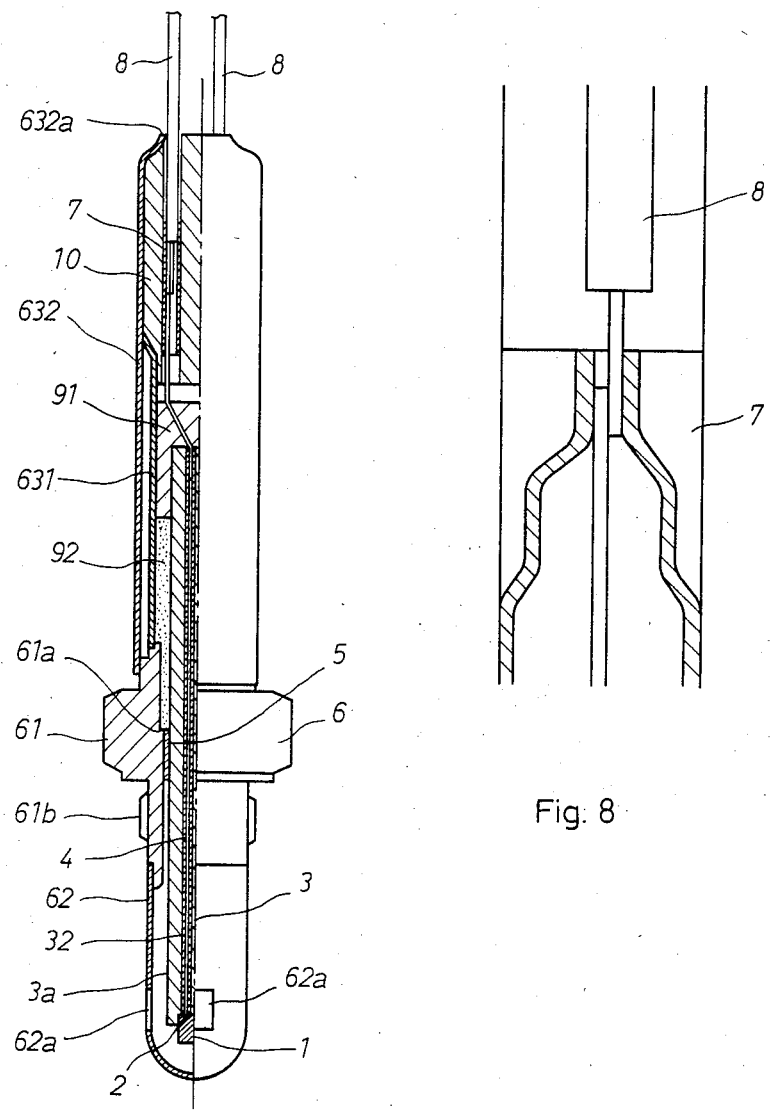
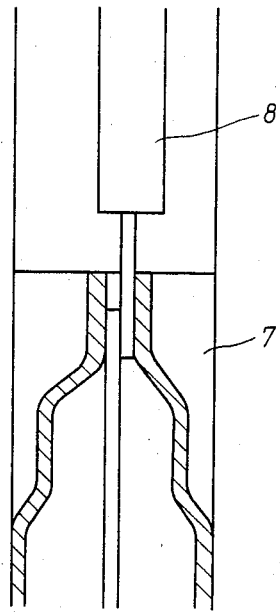
Fig. 7
Fig. 8

GAS COMPONENT DETECTING PLUG

BACKGROUND OF THE INVENTION

(1) Field of Art

The present invention relates to a structure of a gas component detecting plug superior in water resistance and productivity.

(2) Proir Art

For taking out as an electrical output component gases such as combustible gas and oxygen remaining in exhaust gases discharged from various combustion devices, including internal combustion engines and blast furnaces, there has widely been known a gas component detecting plug which employs a gas component-sensitive element (hereinafter referred to simply as "gas-sensitive element") formed of a semiconductor comprising a metal oxide such as $TiO_2$.

Typical examples of this type of gas component detecting plugs include one in which an insulating tube with a gas-sensitive element attached to one end face thereof and with electrode wires connected to the gas-sensitive element and projecting from the opposite head end face through through-holes is sealed to an enclosure, and one in which an insulating board with a gas-sensitive element and electrodes formed on the surface thereof by a thick film printing and interconnected at an end portion by soldering or the like is sealed to an enclosure. In these conventional gas component plugs, in deciding axial or longitudinal and radial or transverse positions of the insulating tube or board (hereinafter referred to simply as "insulator") relative to the enclosure, first the insulator is inserted into the enclosure and then is fixed in a predetermined position by the use of a heat-resisting cement. Further, moisture contained in exhaust gases may get into the interior of the enclosure from the gas-sensitive element side (hereinafter referred to as "leg portion side") and water such as rain water or stagnant water may permeate from the external circuit side, thereby causing a defective insulation especially between electrode wires. To prevent this, there has been adopted a method in which after hardening of the heat-resisting cement, glass is filled into the space surrounding the lead wires from an opening formed in an end portion of the enclosure on the side (hereinafter referred to as "head portion side") opposite to the leg portion side, then a tube formed of rubber, Teflon or the like is inserted and the enclosure is caulked in a radial direction from the outer periphery of the tube. But, such conventional gas component detecting plug involves drawbacks. First, it is difficult to insert the insulator accurately in a predetermined position within the enclosure and to pour the heat-resisting cement uniformly into the gap between the insulator and the enclosure. Secondly, the position of the insulator relative to the enclosure must be temporarily fixed by a mechanical means until the heat-resisting cement hardens, which operation is troublesome. Thirdly, since the heat-resisting cement is poured from the heat portion side opening, it inevitably adheres to the end portion of the insulator on the head portion side and also to the electrode wires, so that the space to be filled with glass in the subsequent step is narrowly limited and a perfect hermetic seal can no longer be expected.

SUMMARY OF THE INVENTION

It is an object of the present invention to provide a gas component detecting plug superior in water resistance and water-proofness.

It is another object of the present invention to provide gas component detecting plug superior in insulating property It is a further object of the present invention to provide a gas component detecting plug which permits an easy insertion of an insulator or pouring of a filler into an enclosure.

It is a still further object of the present invention to provide a gas component detecting plug superior in heat insulating property and gas-tightness.

The gist of the present invention which has been effected in order to achieve the above-mentioned objects resides in a gas component detecting plug in which a tubular or board-like insulator which supports a gas component-sensitive element and lead wires connected thereto is sealed to an enclosure so that the gas component-sensitive element is positioned on the leg portion side, characterized in that a spacer is disposed and retained in the gap between the insulator and the enclosure, a head portion-side space formed by the insulator, enclosure, spacer and electrode wires is filled with glass, and a rubbery elastic member having an insulating property is inserted and sealed into the head portion side.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a quarter-sectional view of a gas component detecting plug according to an embodiment of the present invention;

FIG. 2 is a perspective view of a spacer used therein;

FIG. 4 is a front view showing another example of an insulator;

FIG. 5 is a sectional view taken on line A—A of FIG. 4;

FIG. 6 is a plan view showing another example of an insulator holding portion;

FIG. 7 is a quarter-sectional view of a gas component detecting plug according to a further embodiment of the invention; and FIG. 8 is a partially enlarged view showing another connection of insulated lead wires.

DESCRIPTION OF A PREFERRED EMBODIMENT

Figure 3:
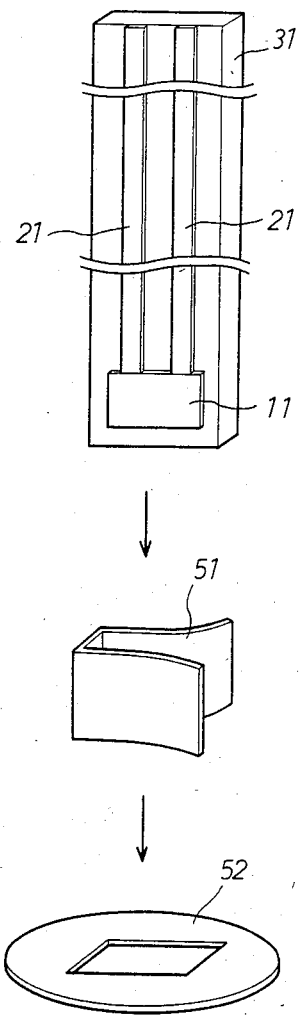
FIG. 3 is a perspective view of an insulator and a spacer used in a gas component detecting plug according to another embodiment of the invention.

The present invention will be described hereinbelow on the basis of embodiments thereof illustrated in the drawings.

Referring first to FIG. 1, the reference numeral 1 denotes a plate-like gas-sensitive element comprising a sintered semiconductor such as $TiO_2$, and a pair of electrode wires 2 comprising fine wires formed of a refractory metal such as platinum or a platinum alloy are oppositely embedded in the interior or sticked or bonded to the surface (not shown) of the gas-sensitive element. The numeral 3 denotes a tubular insulator having through holes 32 for passing therethrough the paired electrode wires 2 projecting from the gas-sensitive element 1 up to the opposite end face. The insulator 3 supports the electrode wires 2 which are bonded to the through holes 32 with a heat-resisting cement 4 and also supports the gas-sensitive element 1 connected to the electrode wires 2.

The numeral 5 denotes a spacer which is formed of stainless steel, soft steel or the like and which is to be fitted on the insulator 3. As shown in FIG. 2 which is an enlarged perspective view of the spacer alone, the spacer 5 comprises an outer edge flange portion 5a formed on the head portion side and inner elastic gripping projections 5b formed on the leg portion side, the inner projections 5b conforming to the outside diameter of the insulator 3 and having elasticity to compensate for variation of the said outside diameter and the flange portion 5a for spacing the insulator 3 from the enclosure 6 in a sealed manner as shown in FIG. 1.

The numeral 6 denotes an enclosure which is formed of a nickel-plated soft steel, stainless steel or the like and which has a reduced inside diameter portion formed on the leg portion side and conforming to the outside diameter of the spacer 5 as well as an enlarged inside diameter portion at least larger than the outer edge portion 5a of the spacer and forming a stepped portion 61a at the boundary with the reduced inside diameter portion. The enclosure 6 comprises a body 61 from which is projecting a leg portion 3a of the insulator 3 for bringing the gas-sensitive element 1 into contact with gas to be detected, the insulator 3 being mechanically fixed by retaining the outer edge portion 5a of the spacer on the stepped portion 61a, and which has a screw portion 61b for threaded engagement with a mounting hole of an exhaust pipe or combustion pipe (not shown) to fix the gas component detecting plug of the present invention to the said pipe; a protective tube 62 which projects from the body 61 and encloses therein and thereby mechanically protects the leg portion 3a of the insulator 3 and the gas-sensitive element 1 and which has a plurality of small holes 62a for allowing gas to be detected to pass therethrough and contact the gas-sensitive element 1; and a tubular shell 63 which surrounds and mechanically protects a head portion 3b of the insulator 3, the electrode wires 2 projecting from the end face of the insulator 3 and the insulated lead wires 8 connected electrically to the electrode wires 2 by caulking terminals 7 or by welding or soldering (not shown).

The numeral 9 denotes glass which is filled into a space formed by the body 61 of the tubular shell 63, spacer 5, head portion 3b of the insulator 3 and the electrode wires 2 projecting from the end face of the head portion of the insulator 3, and then heat-melted and solidified. Before filling of the glass 9, the insulator 3 is mechanically fixed only to the body 61, but the glass 9 once filled strongly bonds the insulator also to the tubular shell 63. Moreover, the glass 9 prevents the moisture contained in exhaust gases from permeating from the leg portion side of the enclosure, particularly through the small holes 62a of the protective tube 62, into the vicinity of the electrode wires 2 projecting from the end face of the head portion of the insulator 3, and it holds the electrode wires in spaced and insulated relation to each other.

The glass 9 before heat melting is usually powder, but there is no fear of its leak to the leg portion side from the spacer 5 during its filling because the spacer 5 is disposed in the gap between the body 61 of the enclosure and the insulator 3.

As the glass 9, i.e. a low melting glass, above all, $PbO\text{-}ZnO\text{-}B_2O_3$ system glass, is easy to handle in view of fluidity and hardenning speed. For example, #7583 glass and #7576 glass both manufactured by Corning Glass Works, U.S.A., are suitable.

The numeral 10 denotes an insulative rubbery elastic member formed of a soft material such as silicone rubber and which is inserted, after solidifying of the glass 9, into the tubular shell 63 with the caulking terminals 7 and insulated lead wires 8 fitted therein. The elastic member 10 prevents water such as rain water or stagnant water from getting into the interior from the head portion side of the enclosure 6. After insertion of the rubbery elastic member 10 into the tubular shell 63, a compressive force is applied thereto from the radial direction by caulking a head portion 63a of the tubular shell 63.

The gas component detecting plug of this embodiment comprises the above basic structure, but various modifications may be made within the scope of its gist, and particularly with respect to such principal portions as the spacer and glass as well as the tubular sell and rubbery elastic member which are closely associated therewith, the following modifications may be made optionally and selectively, all of which ensure the attainment of the objects of the present invention.

The spacer 5, as previously described, is used to compensate for variation in outside diameter of the insulator 3 and fix the insulator 3 to the enclosure 6 mechanically in a simple manner, and to prevent leakage of the glass 9 during filling of the latter. However, its shape need not be restricted to one having the inner projections, 5b; for example, there may be adopted a shape having slits or ribs in place of such inner projections or the inner wall of the axial bore of the body 61 of the enclosure 6 may be tapered in place of the stepped portion 61a to dispense with the outer edge portion 5a. Further, as shown in FIG. 3, where a board-like insulator 31 with a gas-sensitive element 11 and electrodes 21 formed on the surface thereof by a thick film printing is sealed to the enclosure, the spacer is composed of two portions, one of which is an insulator holding portion 51 having two bent arms joined together at one end portion to form a concave transverse section, and the other portion of which is a disc 52 having a central hole conforming to the cross section of the insulator 31 and having an outside diameter conforming to the inside diameter of the axial bore of the body 61 of the enclosure. First, the insulator holding portion 51 is fitted on the insulator 31, then the disc 52 is fitted therebelow on the insulator. Thereafter, the insulator 31 is inserted into the enclosure 6 and the peripheral edge portion of the disc 52 is engaged with the stepped portion 61a in the enclosure 6 or alternatively the tapered portion to fix the insulator 31 to the enclosure, then the glass 9 is filled into the interior of the enclosure. Also in this case, the variation in thickness of the insulator 31 is compensated by the insulator holding portion 51.

As shown in FIG. 4, an insulator 31a may be provided to hold the electrodes 21 between it and the insulator 31.

FIG. 5 is a sectional view taken on line A—A of FIG. 4.

Further, FIG. 6 is a plan view showing another example of the insulator holding portion 51, in which a plurality of projections 51a are formed inside the insulator holding portion 51 so that the insulator 31, insulator holding portion 31a and electrodes 21a may be fixed to the disc 52 more strongly.

The glass 9, as previously noted, is for firmly bonding the insulator to the enclosure and preventing water from permeating into the interior from the leg portion side of the enclosure. But, if the bonding is too strong, a difference in thermal expansion coefficient from the enclosure may cause heat distortion or cracking in the case of exposure to a severe heat cycle environment. This tendency is marked on the leg portion side because the closer to the leg portion, the closer to the exhaust gases and the higher the temperature becomes. Further, the temperature in the vicinity of the spacer 5 becomes high, so after standing for a long time, it is possible that the glass in the vicinity of the spacer 5 will remelt and flow out from the gap between the spacer and the insulator or the enclosure. Therefore, as shown in FIG. 7, it is desirable that the glass 9 be filled only in the vicinity of the electrode wires 2 projecting from the end face of the head portion of the insulator 3 to form a dense portion 91 and that the leg portion side be filled with a composite glass-ceramic sintered mass to form a porous portion 92. Preferably, the ceramic is a powdered heat-resisting ceramic such as powdered alumina, zirconia, mullite, silica or talc, and its content is in the range of 10 to 80 wt. %. If its content is lower than 10 wt. %, it will be less effective for preventing the outflow of glass, and if its content exceeds 80 wt. %, it will be impossible to obtain a porous structure formed by a composite glass-ceramic sintered mass. For example, in the case where talc powder of 100 to 150 mesh is added to #7576 glass manufactured by Corning Glass Works and heat-melted at 500°-550° C. near the pour point of the said glass, a suitable talc content is in the range of 40 to 60 wt. %.

The tubular shell is for mechanically protecting the insulator and glass, but since both the insulator and glass are weak against thermal shock such as covering with water at an elevated temperature, it is desirable that the insulator and the glass be surrounded with a double structure comprising an inner tube 631 and an outer tube 632, with a space being formed therebetween to provide a heat insulating property, as shown in FIG. 7.

The rubbery elastic member 10 is for preventing moisture from getting into the interior from the head portion side, and as shown in the foregoing embodiment, a compressive force may be applied to the insulating tube from the radial direction by caulking the head portion 63a of the tubular shell 63. Alternatively, first the inner tube 631 in such a double structure as mentioned above of the tubular shell is welded to the body 61 of the enclosure with the insulator 3 fixed thereto, and after subsequent, heat melting and solidifying of the glass 9, the caulking terminals 7 and the insulated lead wires 8 are inserted into the rubbery elastic member 10, and finally the outer tube 632 in the form of a sack provided in the head portion thereof with an opening 632a of a size permitting insertion therethrough of the insulated lead wires 8 is fitted over the inner tube and the rubbery elastic member and welded to the body 61. In this case, an axial compressive force is applied to the rubbery elastic member 10, so the rubbery elastic member 10 comes into pressure contact with the enclosure at two points—the edge of its head portion and that of its leg portion—so the water-proofness is improved in comparison with the application of a radial compressive force in which the above pressure contact is made only at one point. In order to facilitate the application of an axial compressive force to the rubbery elastic member, it is desirable that the head portion of the inner tube 631 which contacts the rubbery elastic member be tapered as illustrated, for example.

In FIG. 7, the other portion than the glass, rubbery elastic member and tubular shell is the same as in the embodiment of FIG. 1, so its explanation is here omitted.

As shown in FIG. 8, the insulated lead wires may be bonded in an overlapped state in order to strengthen their bonding, as shown in FIG. 8.

Obviously, numerous modifications and variations of the present invention are possible in light of the above teachings. It is therefore to be understood that within the scope of the appended claims, the invention may be practiced otherwise than as specifically described herein.

What is claimed is:

1. A gas component detecting plug comprising:
    a gas component-sensitive element (1);
    lead wires (2) connected to said gas component-sensitive element (1);
    an insulator (3) which supports both said gas component-sensitive element (1) and the lead wires (2);
    and enclosure (6) in which said gas component-sensitive element (1) and said insulator (3) are sealed so that said gas component-sensitive element (1) is positioned on a leg portion side;
    a spacer (5) which is disposed and retained in a gap formed between said insulator (3) and said enclosure (6) and which further comprises an elastic gripping portion for fixing said insulator (3) in place and a flange portion for spacing said insulator (3) from said enclosure (6) in a sealed manner;
    a glass (9) which fills a space formed by said insulator (3), said enclosure (6), said spacer (5), said lead wire (2) on a head portion side;
    a rubbery elastic member (10) of insulating property which is inserted and sealed in the head portion side.

2. A gas component detecting plug according to claim 1, wherein the enclosure (6) further comprises a body (61), a protective tube (62) and tubular shell (63).

3. A gas component detecting plug according to claim 2, wherein the tubular shell (63) has a double structure comprising an inner tube (631) and an outer tube (632), with a space being formed therebetween, and the insulator and the glass are surrounded with said double structure.

4. A gas component detecting plug according to claim 3, wherein the inner tube (631) is welded to the body (61) of the enclosure with the insulator (3) fixed thereto, and after charge, heat-melting and solidifying of the glass (9), insulated lead wires (8) are inserted into the rubbery elastic member (10), and then the outer tube (632) in the form of a sack provided in the head portion thereof with an opening (632a) of a size permitting insertion therethrough of the insulated lead wires (8) is fitted over the inner tube and the rubbery elastic member and then welded to the body (61).

5. A gas component detecting plug according to claim 4, wherein the head portion of the inner tube (631) in contact with the rubbery elastic member (10) is tapered.

6. A gas component detecting plug according to claim 1, wherein only the vicinity of the electrode wires (2) projecting from an end face of the head portion of the insulator (3) is filled with the glass (9) to form a dense portion (91), and the other portion of the space located therebelow is filled with a composite glass-ceramic sintered mass to form a porous portion (92).

7. A gas component detecting plug according to claim 6, wherein the ceramic consists of a powdered heat-resisting ceramic such as powdered alumina, zirconia, mullite, silica talc, and its content is in the range of 10 to 80 weight percent.

8. A gas component detecting plug according to claim 1, wherein an axial compressive force is applied to the rubbery elastic member (10) and further comprising means to seal said lead wires (2).

9. A gas component detecting plug comprising:
   a gas component-sensitive element (1);
   lead wires (2) connected to said gas component-sensitive element (1);
   a first insulator (3) which supports both said gas component-sensitive element (1) and the lead wires (2); and enclosure (6) in which said gas component-sensitive element (1) and said first insulator (3) are sealed so that said gas component-sensitive element (1) is positioned on a leg portion side;
   a spacer (5) which is disposed and retained in a gap formed between said first insulator (3) and said enclosure (6) and which further comprises an elastic gripping portion for fixing said first insulator (3) in place and a flange portion for spacing said first insulator (3) from said enclosure (6) in a sealed manner;
   a glass (9) which fills a space formed by said first insulator (3), said enclosure (6), said spacer (5), said lead wire (2) on a head portion side;
   a rubbery elastic member (10) of insulating property which is inserted and sealed in the head portion side; and
   wherein the enclosure (6) further comprises a body (61), a protective tube (62) and tubular shell (63);
   further comprising means for sealing said first insulator (31) with a gas-sensitive element (11) and electrodes (21) formed on the surface thereof by a thick film printing to the enclosure and wherein the spacer further comprises two parts one of which is an insulator holding portion (51) having two bent arms joined at one end portion to form an concave transverse section and the other of which is a disc (52) having a central hole conforming to the transverse section of the insulator (31) and having an outside diameter conforming to the inside diameter of an axial bore of a body (61) of the enclosure.

10. A gas component detecting plug according to claim 9, further comprising a second insulator (31a) means for holding the electrodes (21) between the first insulator (31) and said second insulator (31a).

11. A gas component detecting plug according to claim 9, further comprising means for fitting the insulator holding portion (51) on the insulation (31), for fitting the disc (52) therebelow on the first insulator (31), for inserting the first insulator (31) into the enclosure (6) until the peripheral edge portion of the disc (52) comes into engagement with a stepped portion (61a) or a tapered portion in the enclosure (6) to fix the first insulator (31) to the enclosure, and for charging the glass (9) into the space on the head portion side.

12. A gas component detecting plug according to claim 11, wherein the insulator holding portion (51) has a plurality of projections (51a) formed on its inside.

* * * * *